United States Patent [19]

Foss

[11] Patent Number: 5,351,866
[45] Date of Patent: Oct. 4, 1994

[54] VIAL HOLDERS

[76] Inventor: Delbert Foss, N. 5208 Millview Dr., Spokane, Wash. 99212

[21] Appl. No.: 61,209

[22] Filed: May 13, 1993

[51] Int. Cl.⁵ .............................................. A45C 11/00
[52] U.S. Cl. .................................... 224/218; 224/148; 224/247
[58] Field of Search .............. 224/218, 217, 219, 267, 224/148, 222, 247, 907

[56] References Cited

U.S. PATENT DOCUMENTS

| | | | |
|---|---|---|---|
| 1,139,942 | 5/1915 | Wightman et al. | 223/109 |
| 1,462,714 | 7/1923 | Marchand | 224/217 X |
| 1,766,478 | 6/1930 | Baker et al. | 224/218 |
| 1,976,653 | 10/1934 | Brueck | 224/217 |
| 2,072,851 | 3/1937 | Bailey | 224/217 X |
| 2,084,343 | 6/1937 | Jefferis | 224/217 X |
| 2,140,231 | 12/1938 | Jefferis | 224/217 |
| 2,165,625 | 7/1939 | Fessel | 224/219 |
| 2,222,741 | 11/1940 | Bush | 224/217 |
| 2,356,722 | 8/1944 | Harris | 224/217 |
| 2,613,110 | 10/1952 | Spingarn | . |
| 3,666,372 | 5/1972 | Lipkowski | 224/217 X |
| 4,477,005 | 10/1984 | Martinez | 224/218 |
| 4,606,484 | 8/1986 | Winter et al. | 224/218 |
| 4,928,864 | 5/1990 | Walker et al. | 224/162 |
| 5,016,795 | 5/1991 | Porteous | 224/217 |
| 5,112,227 | 5/1992 | Bull | 433/163 |
| 5,215,236 | 6/1993 | Waddell | 224/218 |

FOREIGN PATENT DOCUMENTS 931816 3/1948 France .................. 224/219

Primary Examiner—Renee S. Luebke
Attorney, Agent, or Firm—Wells, St. John, Roberts, Gregory & Matkin

[57] ABSTRACT

A vial holder has a handle portion adapted to be carried by a human hand and a friction mount for releasibly retaining a vial. The friction mount is fixedly coupled to the handle portion. The handle portion and friction mount are formed as first and second "C"-shaped members that are integrally connected back-to-back so that the first and second "C"-shaped members open in opposite directions. The "C"-shaped members are oriented perpendicularly to one another so that the vial, when positioned in the holder, is aligned approximately 90° relative to the user'hand as it grasps the holder. A method for producing the vial holder is also described.

The method includes the steps of (a) providing a cross-shaped piece of material having opposing ends and opposing flanges; (b) folding the opposing ends in a first direction; (c) shaping the opposing ends about corresponding end axes to form a handle adapted to received fingers of a human hand; (d) folding the opposing flanges in a second direction opposite to the first direction; and (e) shaping the opposing flanges about a longitudinal axis to form a mount adapted to receive a vial.

12 Claims, 4 Drawing Sheets

VIAL HOLDERS

TECHNICAL FIELD

This invention relates to vial holders. This invention also relates to methods for producing vial holders.

BACKGROUND OF THE INVENTION

Medicine is commonly supplied in the form of a serum. The serum is distributed in small plastic or glass vials. Individual vials have a cap with a membrane that permits insertion of a hypodermic needle to extract the serum, but prevents leakage of the serum after the needle is withdrawn.

For some treatments, the patients themselves administer the serum. For example, diabetics are given hypodermic needles and vials of insulin to self-administer the proper dosages. A problem arises for certain patients that have difficulty holding the vials. An elderly patient, or one with arthritis, often have trouble steadying the vial for insertion of the needle.

U.S. Pat. No. 4,606,484 to Winter et al. discloses a tool for holding common utensils (tooth brush, spoon, floss holder) that can be used by persons with limited use of their hands. The tool includes a socket base that is rotatably mounted within a fixed housing. An O-ring is fitted between the socket base and the housing to provide frictional holding force while allowing a snap-out, snap-in disassembly for cleaning. The tool also includes a strap that is looped through the fixed housing to fasten the device to a user's hand. The strap has the added function of retaining the socket base within the fixed housing.

It is first noted that the tool of the '484 patent is not designed to hold vials. Additionally, modification of the tool still would not provide a suitable vial holder. First, the socket base is rotatably mounted. This is a significant drawback when attempting to steady the vial for insertion of the hypodermic needle because the vial is likely to move causing the patient to miss and accidently stick his/her hand with the needle. Second, the strap is difficult to fasten, particularly for those with limited use of their hands. Third, the tool is complex with many parts, resulting in higher manufacturing costs.

This invention provides a simple and cost-effective device for holding vials.

BRIEF DESCRIPTION OF THE DRAWINGS

Preferred embodiments of the invention are described below with reference to the following accompanying drawings.

FIG. 8 is a perspective view of the preformed vial holder and illustrates a step of shaping a handle portion. FIG. 9 is a perspective view of a partially formed vial holder and illustrates a step of shaping a friction mount portion.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
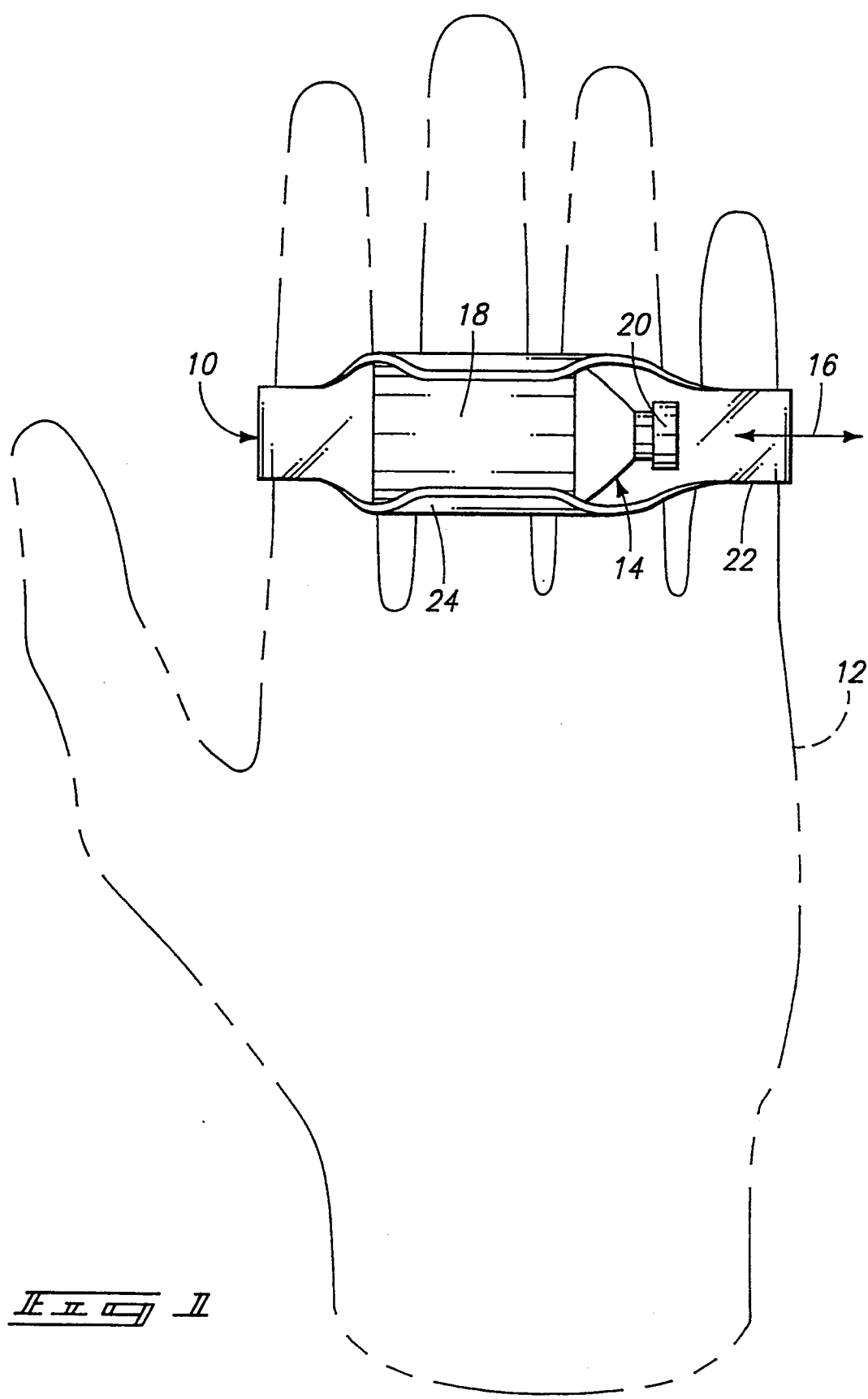
FIG. 1 is a top view illustration of a vial holder and vial of this invention being held by a user.

FIG. 1 shows a vial holder 10 being held by a human hand 12. The vial holder 10 releasibly retains a vial 14 that contains a liquid, such as serum (e.g., insulin). Vial 14 is alternately inserted into, and removed from, the vial holder 10 as indicated by arrow 16. Vial 14 has a body 18 which tapers through a neck portion to a cap 20. Vial 14 is of conventional design and is not described in detail.

Vial holder 10 includes a handle portion 22 that is adapted to be carried by human hand 12. Handle portion 22 is sized to fit across multiple fingers. In this example, the handle portion 22 extends across and is held by four fingers. Other grasping arrangements are possible, such as holding the vial holder 10 between the thumb and the forefinger.

Vial holder 10 has a mount portion 24 for releasibly retaining vial 14. Mount portion 24 is sized to accommodate the body 18 of vial 14. More specifically, mount portion 24 defines a substantially cylindrical cavity with a cross-sectional area that is slightly less than the cross-sectional area of body 18. Mount 24 has sides which are slightly resilient and expand upon insertion of vial 14. The vial is held under the force of friction between the sides of mount 24. Additionally, the friction mount 24 has a contour with sloping edges on one end thereof to aid in guiding the vial 14 into, and out of, the cylindrical cavity.

Friction mount 24 is fixedly coupled to handle portion 22 and does not rotate relative thereto. The non-rotation feature is advantageous because it allows the user to steady the vial, and maintain its alignment, while inserting the hypodermic needle. In the preferred form, handle portion 22 and mount portion 24 of vial holder 10 are integrally formed of a single piece of material. However, in other embodiments, the handle portion and friction mount can be manufactured separately and connected together.

Another advantage of this invention is that handle portion 22 operates as a shield to protect the fingers from being pricked by the needle in the event that the user accidently misses during needle insertion. The material of the handle has sufficient thickness to prevent puncture therethrough by the needle.

Figure 2:
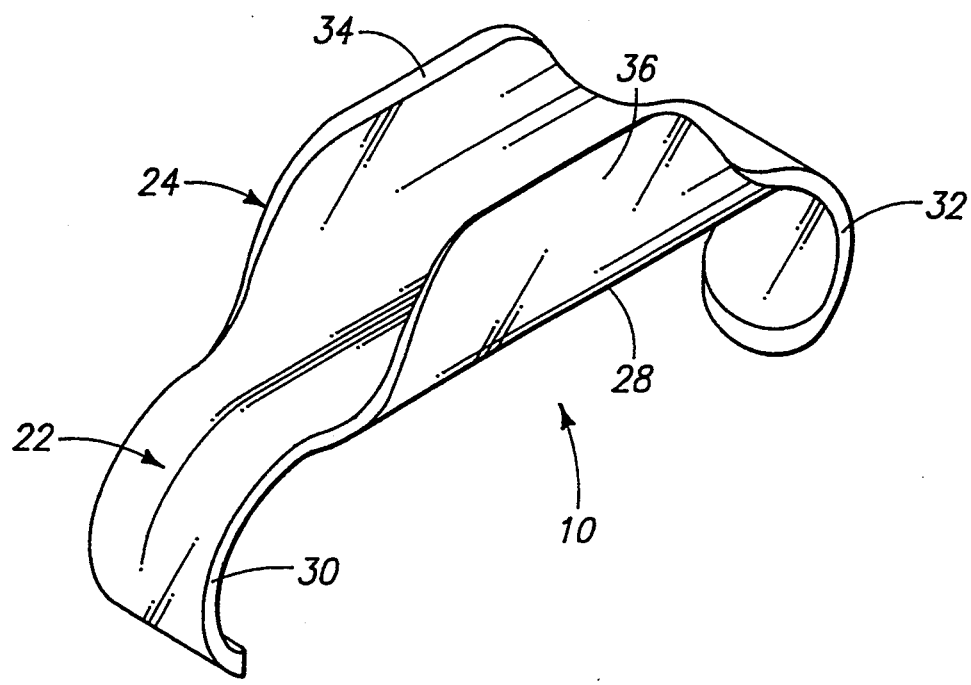
FIG. 2 is a perspective view of the vial holder.
Figure 3:
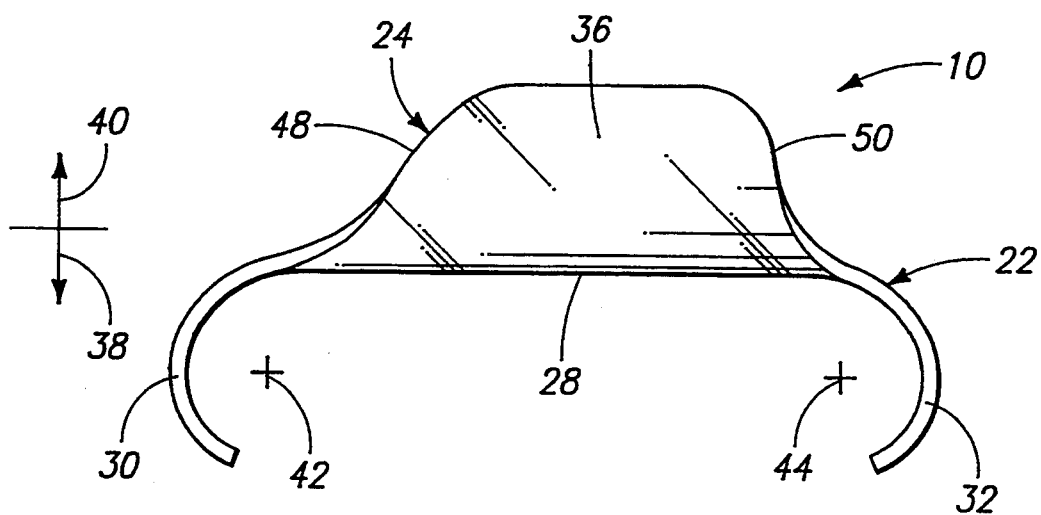
FIG. 3 is a side view of the vial holder.
Figure 4:
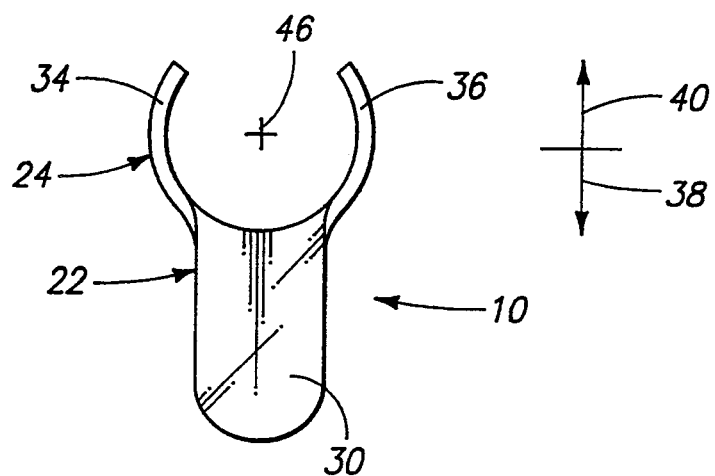
FIG. 4 is an end view of the vial holder.

FIGS. 2–6 show the vial holder 10 in more detail. Handle portion 22 is configured as an inverted or first "C"-shaped member, as best shown in FIG. 3. Similarly, friction mount 24 is configured as a second "C"-shaped member, as shown in FIG. 4. The two "C"-shaped members are connected or integrally formed back-to-back so that the "C"-shaped members open in opposing directions (FIG. 2). The two "C"-shaped members are oriented substantially perpendicular relative to one another. In this construction, the vial 14 is held approximately 90° relative to hand 12 (FIG. 1) to facilitate easy and efficient serum extraction from the vial.

In the most preferred form, vial holder 10 is formed of an integral piece of plastic. Vial holder 10 has a middle section 28, a first end 30, and a second end 32. Vial holder 10 also includes a first flange or side 34 and a second flange or side 36 on opposing sides of the middle section 28. The first and second ends 30, 32 curve away from middle section 28 to extend in a first direction (as represented by arrow 38 in FIGS. 3 and 4), whereas the first and second sides 34, 36 curve away from the middle section 28 to extend in an opposing second direction (as represented by arrow 40).

The first and second ends 30, 32 have a semi-annular shape to accommodate the fingers of the user's hand 12. More specifically, first end 30 curves partially around, and is radially spaced from, a first axis 42. Similarly, second end 32 wraps partially around, and is radially spaced from, second axis 44. The axes 42 and 44 are spaced apart from, and substantially parallel to, one another (FIG. 5).

The first and second sides 34, 36 are shaped to hold a vial. The sides are semi-annular and define a substantially cylindrical cavity for receiving and frictionally retaining the cylindrical-shaped body 18 of vial 14. Sides 34, 36 are formed about a longitudinal third axis 46 that is at the center of the cavity. Vial holder 10 is preferably configured such that third axis 46 is substantially perpendicular to first and second axes 42, 44 (FIG. 5).

Figure 5:
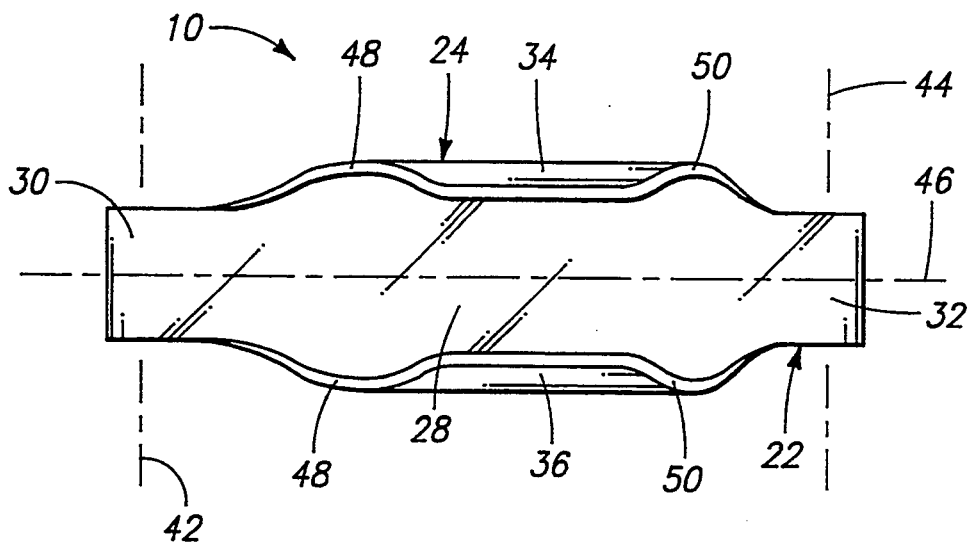
FIG. 5 is a top view of the vial holder.
Figure 6:
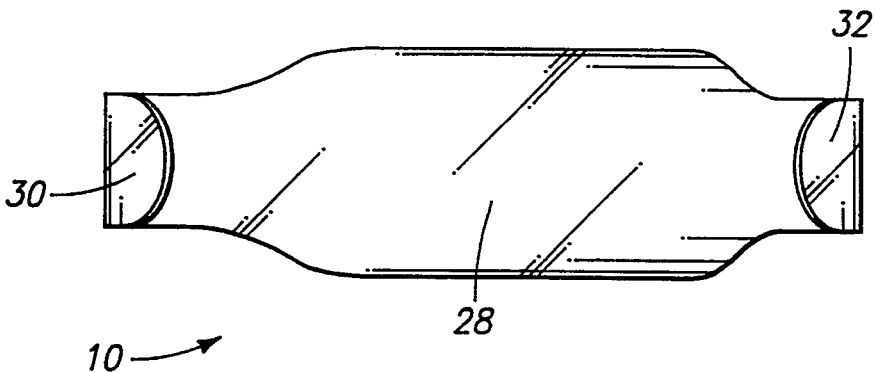
FIG. 6 is a bottom view of the vial holder.

Sides 34, 36 have first edges 48 which slope outwardly from first end 30 (FIGS. 3 and 5). This smooth contour aids in directing the vial into the cavity of the holder. The sides 34, 36 also have second edges 50 which are relatively straight and sire aligned nearly perpendicularly relative to the longitudinal axis of the vial holder.

Figure 7:
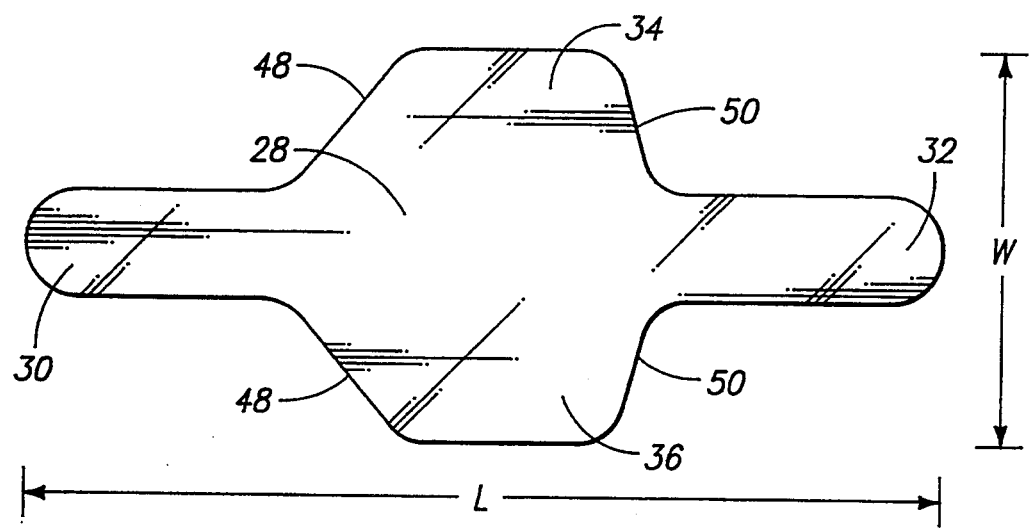
FIG. 7 is a top view of a pre-formed vial holder.

The vial holder 10 can be sized accordingly to fit various human hands. In the preferred embodiment of FIG. 7, the length L of the holder (measured from first end 30 to second end 32) is at least twice the width W (measured from the first side 34 to the second side 36). As an example, length L is approximately 4–6 inches and width W is approximately 2–3 inches.

As above, the vial holder is preferably formed of plastic. An example material is PLEXIGLASS. However, other types of material can be used, such as metal. The material should be moldable or malleable so that it can be shaped from a flat unit into the desired shape. Alternatively, the vial holder 10 could be formed through injection molding. However, the material should possess sufficient rigidity to maintain the desired friction force on the vial without deforming or permanently bending.

Additionally, a combination of materials can be used. For example, a special friction surface can be applied along the inner surface of sides 34 and 36 to provide a mount with a higher friction coefficient. As another example, soft material, such as felt, could be added along the bottom surface of middle section 28 and ends 30, 32 to promote comfort on the user's hand.

Figure 8:
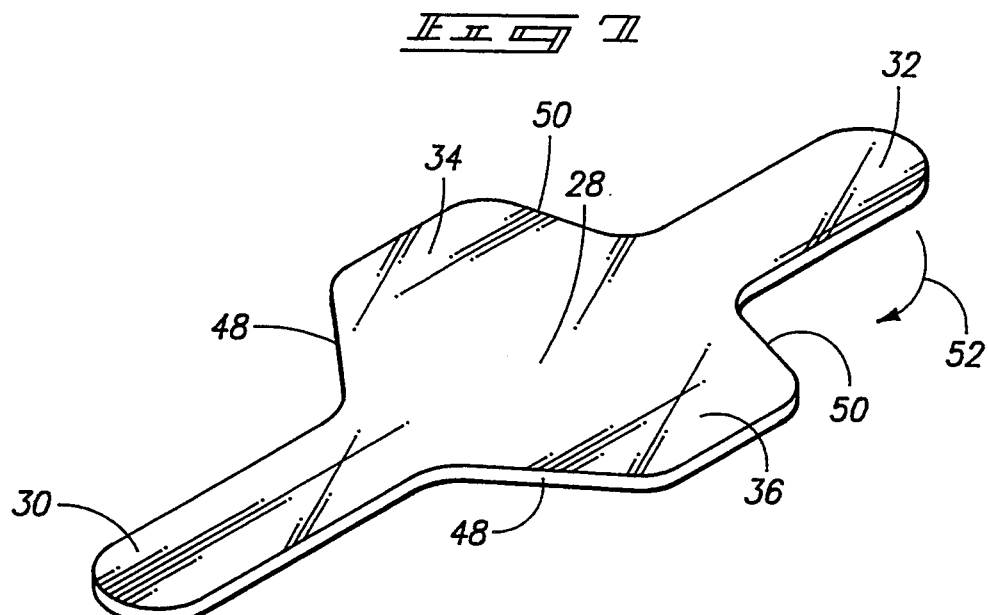
FIGS. 8 and 9 illustrate a method for forming a vial holder according to this invention.
Figure 9:
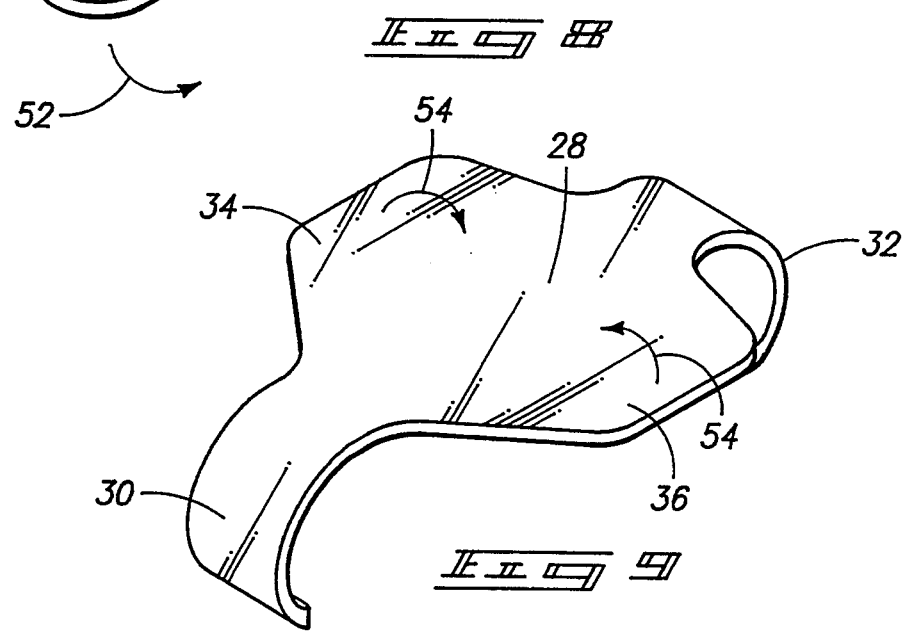

According to another aspect of this invention, a method for producing a vial holder will now be described with reference to FIGS. 8 and 9. Initially, a piece of material is cut and formed into a cross-shaped unit as depicted in FIG. 8. For example, the unit can be cut via a jigsaw, or the like, from a larger sheet of material (such as PLEXIGLASS). The edges of the cut unit are then sanded or otherwise machined to make them smooth.

The unit has opposing ends 30 and 32 and opposing flanges or sides 34 and 36. Preferably, the unit has a contour wherein flanges 34, 36 have sloping edges 48 and relatively straight, perpendicular edges 50 provided on opposing ends thereof.

Ends 30 and 32 are folded downward in the first direction as indicated by arrows 52 to form a first "C"-shaped member. The ends are curved or otherwise shaped radially about their respective central axes 42 and 44 to form a handle adapted to receive the user's fingers. Next, flanges 34 and 36 are folded upward in the second direction as indicated by arrows 54 to form a second "C"-shaped member. The flanges are likewise curve or otherwise shaped about the longitudinal central axis 46 to define a cavity sized to receive a vial. The resulting vial holder is illustrated in FIGS. 2–6.

The above sequence of steps is provided for purposes of explanation. The process of this invention may be conducted according to steps in a different order. For example, flanges 34 and 36 can be folded and shaped prior to folding and shaping ends 30 and 32.

This invention is advantageous in that it provides a simple tool for holding vials. It has only one part, making it easy to manufacture, use, and clean. Moreover, the vial holder is inexpensive to produce.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A vial holder comprising:
    a handle portion adapted to be carried by a human hand, the handle portion comprising an inverted first "C"-shaped member; and
    a mount portion for releasibly retaining a vial, the mount portion comprising a second "C"-shaped member fixedly coupled to the inverted first "C"-shaped member of the handle portion so that the first and second "C"-shaped members open in opposite directions, the first and second "C"-shaped members being oriented substantially perpendicular to one another.

2. A vial holder according to claim 1 wherein the handle portion and the mount portion are integrally formed of a single piece of material.

3. A vial holder according to claim 1 wherein the handle portion and the mount portion are integrally formed of a single piece of plastic.

4. A vial holder according to claim 1 wherein:
    the "C"-shaped handle portion comprises first and second semi-annular ends; and
    the "C"-shaped mount portion comprises first and second semi-annular sides that define a substantially cylindrical cavity for receiving the vial.

5. A vial holder according to claim 1 wherein:
    the "C"-shaped handle portion comprises first and second semi-annular ends that curve partially around first and second axes, the first axes being spaced from, and substantially parallel to, the second axis; and
    the "C"-shaped mount portion comprises first and second semi-annular sides that define a substantially cylindrical cavity for receiving the vial, the sides being provided around a longitudinal axis that is substantially perpendicular to the first and second axes.

6. A vial holder comprising:

an integral piece of material having a middle section, first and second ends on opposing ends of the middle section, and first and second sides on opposing sides of the middle section;

the first and second ends curving from the middle section to extend in a first direction, individual first and second ends having a semi-annular shape to accommodate a user's fingers, the first and second semi-annular ends having respective first and second axes which are spaced from, and substantially parallel to, one another; and the first and second sides curving from the middle section to extend in a second direction opposite to the first direction, the first and second sides being shaped to hold a vial, the first and second sides defining a third axis that is substantially perpendicular to the first and second axes.

7. A vial holder according to claim 6 wherein the integral piece of material comprises plastic.

8. A vial holder according to claim 6 wherein the first and second sides are semi-annular and define a substantially cylindrical cavity.

9. A vial holder according to claim 6 wherein the integral piece has a length from the first end to the second end and a width from the first side to the second side, the length being at least twice the width.

10. An apparatus comprising:

a vial for holding a liquid; and a vial holder, the vial holder comprising:

a handle portion adapted to be carried by a human hand, the handle portion comprising an inverted first "C"-shaped member; and a mount portion for releasibly retaining the vial, the mount portion comprising a second "C"-shaped member fixedly coupled to the inverted first "C"-shaped member of the handle portion so that the first and second "C"-shaped members open in opposite directions, the first and second "C"-shaped members being oriented substantially perpendicular to one another.

11. An apparatus according to claim 10 wherein the vial holder is formed of a single piece of material.

12. A vial holder according to claim 10 wherein:

the "C"-shaped handle portion comprises first and second semi-annular ends that curve partially around first and second axes, the first axes being spaced from, and substantially parallel to, the second axis; and the "C"-shaped mount portion comprises first and second semi-annular sides that define a substantially cylindrical cavity for receiving the vial, the sides being provided around a longitudinal axis that is substantially perpendicular to the first and second axes.

* * * * *